(12) United States Patent
Borody

(10) Patent No.: US 9,399,106 B2
(45) Date of Patent: Jul. 26, 2016

(54) MASK FOR USE WITH A PATIENT UNDERGOING A SEDATED ENDOSCOPIC PROCEDURE

(75) Inventor: Thomas Julius Borody, Five Dock (AU)

(73) Assignee: Thomas Julius Borody, Five Dock (AU)

( * ) Notice: Subject to any disclaimer, the term of this patent is extended or adjusted under 35 U.S.C. 154(b) by 831 days.

(21) Appl. No.: 13/522,015

(22) PCT Filed: Nov. 25, 2010

(86) PCT No.: PCT/AU2010/001583
§ 371 (c)(1),
(2), (4) Date: Sep. 10, 2012

(87) PCT Pub. No.: WO2011/085427
PCT Pub. Date: Jul. 21, 2011

(65) Prior Publication Data
US 2012/0330111 A1    Dec. 27, 2012

(30) Foreign Application Priority Data

Jan. 13, 2010    (AU) ................................ 2010900118

(51) Int. Cl.
*A61M 16/06*    (2006.01)
*A61M 16/04*    (2006.01)

(52) U.S. Cl.
CPC ....... *A61M 16/0683* (2013.01); *A61M 16/0488* (2013.01); *A61M 16/0493* (2014.02); *A61M 16/0666* (2013.01); *A61M 2205/18* (2013.01); *A61M 2230/205* (2013.01); *A61M 2230/42* (2013.01); *A61M 2230/432* (2013.01)

(58) Field of Classification Search
CPC ..................... A61M 16/0488–16/0497; A61M 16/06–16/0655; A61M 16/0683
See application file for complete search history.

(56) References Cited

U.S. PATENT DOCUMENTS

| | | | | |
|---|---|---|---|---|
| 2,382,364 A | * | 8/1945 | Yant ....................... | A62B 18/02 128/201.19 |
| 4,470,413 A | * | 9/1984 | Warncke .................. | 128/201.18 |
| 5,431,158 A | * | 7/1995 | Tirotta ..................... | 128/206.21 |
| 5,513,634 A | | 5/1996 | Jackson | |
| 5,694,929 A | * | 12/1997 | Christopher ............. | 128/207.14 |
| 6,055,981 A | * | 5/2000 | Laswick et al. .......... | 128/204.18 |
| 6,626,177 B1 | * | 9/2003 | Ziaee ....................... | 128/206.21 |
| 6,736,139 B1 | | 5/2004 | Wix | |
| 6,758,212 B2 | * | 7/2004 | Swann ..................... | 128/201.25 |
| 7,121,279 B2 | * | 10/2006 | Dennis .................. | A61M 16/06 128/203.29 |
| 8,893,719 B2 | * | 11/2014 | Lavi et al. ................ | 128/206.29 |

(Continued)

FOREIGN PATENT DOCUMENTS

| CN | 201175514 Y | 1/2009 |
|---|---|---|
| DE | 3543931 A1 | 6/1987 |

(Continued)

*Primary Examiner* — Valerie L Woodward
(74) *Attorney, Agent, or Firm* — McDermott Will & Emery LLP

(57) ABSTRACT

A face mask (10) for a patient undergoing a sedated endoscopic procedure. The face mask (10) includes at least one of a duct or an aperture (16, 17) to provide positive airway pressure to the nose, a bite block (18) with an opening therein (20) and a one-way valve (22). The one-way valve (22) has an open position, allowing passage of an endoscopic device therethrough and into the opening (20), and a closed position substantially sealing the opening (20).

35 Claims, 3 Drawing Sheets

(56) References Cited

U.S. PATENT DOCUMENTS

| | | | |
|---|---|---|---|
| 2003/0024530 A1* | 2/2003 | Sniadach | 128/202.28 |
| 2003/0047189 A1* | 3/2003 | Kumar et al. | 128/206.29 |
| 2006/0118117 A1* | 6/2006 | Berthon-Jones et al. | 128/206.21 |
| 2006/0207597 A1 | 9/2006 | Wright | |
| 2007/0068535 A1 | 3/2007 | Colman et al. | |
| 2007/0272249 A1* | 11/2007 | Chandran et al. | 128/206.28 |
| 2009/0000621 A1* | 1/2009 | Haggblom et al. | 128/205.12 |
| 2009/0275851 A1* | 11/2009 | Colman et al. | 600/532 |
| 2010/0326435 A1 | 12/2010 | Filipi | |
| 2011/0162647 A1* | 7/2011 | Huby et al. | 128/203.14 |
| 2011/0232647 A1* | 9/2011 | Ho | A61M 16/06 128/206.28 |

FOREIGN PATENT DOCUMENTS

| | | |
|---|---|---|
| JP | 2003-516825 A | 5/2003 |
| JP | 2007-500566 A | 1/2007 |
| JP | 2011-515153 A | 5/2011 |
| WO | WO-01/43804 A1 | 6/2001 |
| WO | WO-2007/063532 A2 | 6/2007 |
| WO | WO-2009/066277 A1 | 5/2009 |
| WO | WO-2009/117422 A2 | 9/2009 |

* cited by examiner

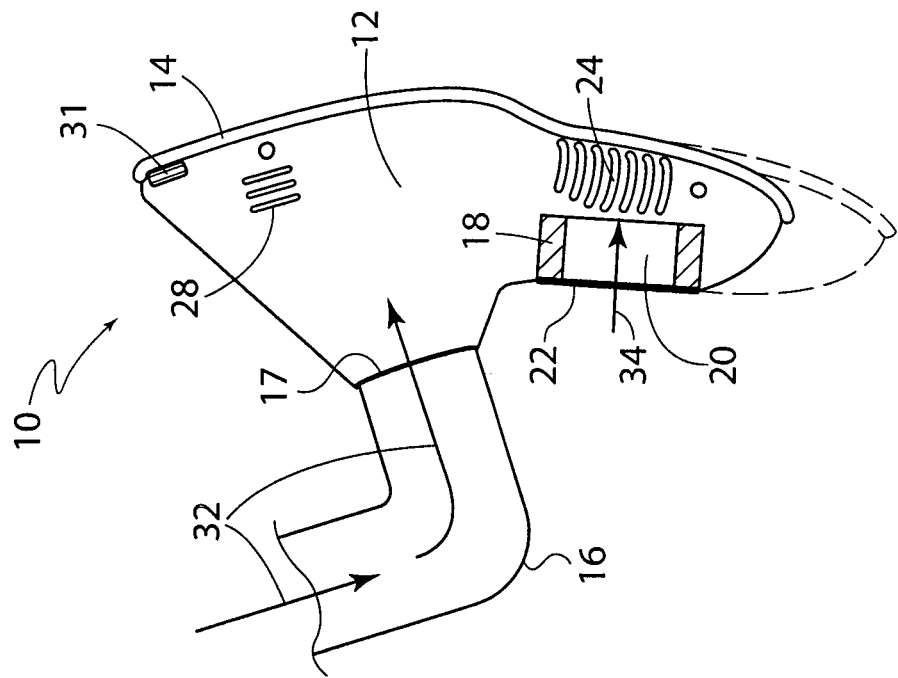
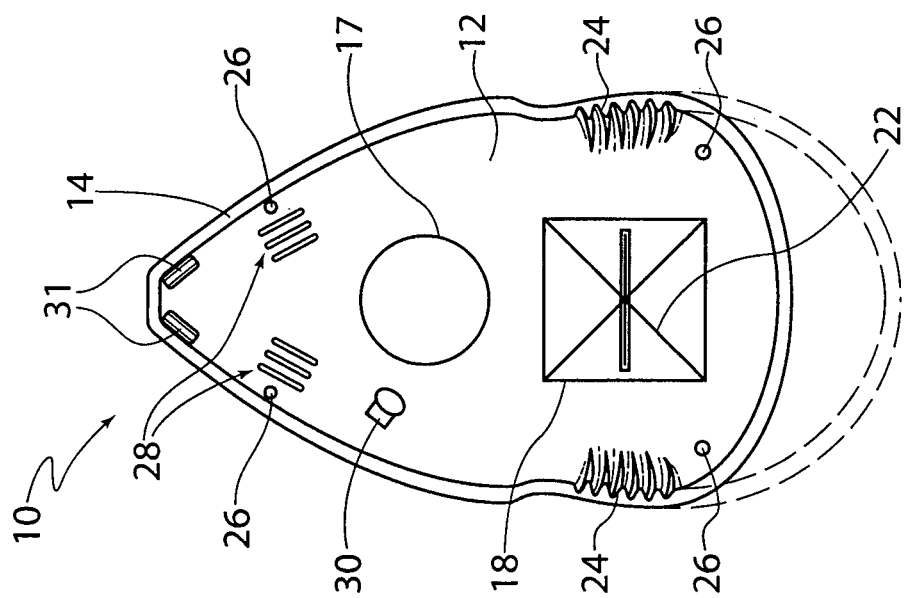

MASK FOR USE WITH A PATIENT UNDERGOING A SEDATED ENDOSCOPIC PROCEDURE

FIELD OF THE INVENTION

The present invention relates generally to a mask for use with a patient undergoing a sedated endoscopic procedure (variously termed 'gastroscopy', panendoscopy, oesophago-gastro-duodenoscopy, or bronchoscopy).

More particularly, the present invention relates to a mask which can facilitate delivery of gases during endoscopic sedation as well as permitting positive pressure ventilation of an over-sedated patient. In a preferred form, the mask also permits measurement of a patient's oxygen and $CO_2$.

BACKGROUND OF THE INVENTION

Patients are frequently investigated using endoscopic devices in order to diagnose conditions of the stomach which may cause them symptoms. Such conditions may include peptic ulcers, reflux oesophagitis, stomach cancer and lung diseases among other numerous diagnoses.

Oesophagogastro-duodenoscopy, also called gastroscopy, generally requires the patient to: (1) be sedated; (2) have their mouth open by a specialized bite block; and (3) be oxygenated during endoscopy because the procedure sometimes induces hypoxia (low oxygen tension in the blood and tissues). This similarly applies to bronchoscopy as a procedure.

Hypoxia can be of critical importance if the patient does not breathe adequately to maintain oxygen tension, as prolonged low oxygen tension can lead to abnormal heart rhythm, cardiac and respiratory arrest, leading to death. Oxygen tension is currently measured by pulse oximetry and ventilation is achieved by the patient breathing spontaneously as in a deep sleep.

At the clinical level, during endoscopic procedures, every effort is made to ensure sedated patients are adequately ventilated with the aim of oxygen tensions being kept well above 90%. However, due to known patient clinical variability (anatomical differences, such as short neck, inter-current illness, such as emphysema, and past sedative drug use) sedation requirements vary markedly from patient to patient. Hence, it is quite often very difficult, when using higher drug doses, to have the patient adequately sedated and still expect to see spontaneous respiration to a level where the oxygen tension is above 90%. As a result, and not infrequently, patients' oxygen tension dips well below 90% and in some situations patients may end up with respiratory arrest as a complication of endoscopic sedation. Indeed, hypoxia during endoscopy has been referred to by some as 'Iatrogenic Sleep Apnoea'.

Idiopathic Sleep Apnoea (or Obstructive Sleep Apnoea—OSA) is a common condition in the community where, during sleep, the patient breathes less frequently and/or deeply than the required amount and the oxygen tension can drop to dangerously low levels of even 70% or so, and on rare occasions, down to 55%. Repetitive night apnoea of more than 10 seconds per episode (and up to 2 minutes of apnoea) can be recorded during sleep studies in such patients. These are dangerous levels which can have multiple long term consequences, including hypertension, daytime somnolence, pulmonary hypertension, coronary and cerebrovascular disease and cardiac arrhythmias among others.

During endoscopy or bronchoscopy patients who are ill are being investigated and acute hypoxia induced by sedation which can reproduce 'sleep apnoea', can have serious complications including respiratory arrest, cardiac arrest and/or death.

It is therefore of importance to ensure patients are well ventilated and oxygenated, and with airway obstruction prevented wherever possible. On occasions, excessive sedation can induce prolonged apnoea, at times requiring manual ventilation. This is a common enough complication for it to lead to emergency situations and on rare occasions, can result in the death of the patient undergoing an endoscopic examination.

Australian Patent Number 634847 discloses a bite block which oxygenates patients, in order to reduce hypoxic complications of endoscopic sedation. PCT publication no. WO 2001/095971 discloses another oxygenating device, which delivers oxygen mainly via the nose. However, neither of these devices is able to adequately ventilate a patient at a time when he/she is deeply sedated while undergoing often a prolonged procedure. U.S. Pat. No. 6,792,943 discloses a face mask which can ventilate patients for a short time while they are being rapidly intubated. The disclosed mask has two ports, one for intubation of the trachea and another for supply of oxygenation gas under pressure to both nose and mouth. However, given the variability of facial structure and shape, the disclosed mask lacks the ability to obtain a tight enough seal to achieve positive pressure ventilation, which is crucial for intubation.

It is an object of the present invention to substantially overcome or at least ameliorate one or more of the above deficiencies.

SUMMARY OF THE INVENTION

Accordingly, the present invention provides a face mask for a patient undergoing a sedated endoscopic procedure, the face mask includes:
  means to provide positive airway pressure to the nose;
  a bite block with an opening therein; and
  a one-way valve having an open position, adapted to allow passage of an endoscopic device therethrough and into the opening, and a closed position substantially sealing the opening.

In one form, the face mask includes a body adapted to cover the patient's nose and mouth in a substantially sealed relationship with the patient's skin. In this form, the means to provide positive airway pressure to the nose and the bite block are attached to, or form part of, the body.

In another form, the face mask includes a first body adapted to cover the patient's nose in a substantially sealed relationship with the patient's skin and a second body adapted to cover the patient's mouth in a substantially sealed relationship with the patient's skin. In this form, the means to provide positive airway pressure to the nose is attached to, or forms part of, the first body and the bite block is attached to, or forms part of, the second body.

The mask preferably includes one or more straps for securing the mask to the patient's head. The straps are preferably length adjustable or elastic, in order to allow the mask to be pressed against the patient's skin to improve sealing.

The mask preferably includes one more sealing elements around its periphery adapted to form a substantially sealed relationship with the patient's skin. In one form, the sealing element includes a hollow, tubular rubber rim or similar multiple soft rubber rims. The sealing element can also include openings allowing suction against the patient's skin, via a negative pressure being maintained within the interior of the sealing element.

The means to provide positive airway pressure to the nose preferably includes a port or aperture adjacent, in use, the patient's nose or right hand side of the patient's face, the port or aperture being adapted for fluid communication with a manual source or an automated source of positive pressure. The port or aperture is preferably adapted for connection directly to a Continuous Positive Airway Pressure (CPAP) automatic ventilating device or to a vent or bag valve mask ventilation system (e.g. a Leardal bag). The CPAP device is preferably flow rate and pressure adjustable. The CPAP device can include disposable intranasal CPAP bumpers.

The source of positive pressure preferably includes a re-breathing valve system to allow exhalation. The source of positive pressure preferably includes a sensing device adapted to signal a need for manual ventilation or to automatically activate the CPAP device at a pre-arranged ventilation frequency, oxygen tension, and/or $CO_2$ level trigger point. The source of positive pressure preferably includes a CPAP device used as a passively ventilating nasal system with manual and automatic CPAP override.

The bite block opening is preferably adapted to accommodate an endoscope. The bite block can be disposable or reusable.

The one-way valve preferably includes a substantially circular doughnut-like balloon. Alternatively, the one-way valve can be a rubber membrane with a central round opening sized to admit an endoscope. The rubber membrane opening is preferably of a size just smaller than an endoscope. The rubber membrane opening can also be sized to suit a larger instruments, for example a 60 French boogie or a dilator, for patients who have an oesophageal structure in need of dilatation. The opening can be lubricated to permit the smoother entry of an endoscope and/or to also prevent retrograde escape of oxygen during the patient's positive pressure oxygenation. The sealing of the opening also, during endoscopy, prevents inhalation of oxygen-poor room air.

The one-way valve can be of several types, including a Heimlich-type valve. The Heimlich-type valve can be in the form of a disposable condom-type device, which is attached to the bite block adjacent the opening. In this way, the one-way valve does not have to be autoclaved but can be changed between patients and will not be damaged with reuse. A fixed Heimlich-type valve can be used and re-washed but it is preferable to use for the disposable condom-type device to reduce cross infection.

Alternatively, the one-way valve can be a fixed doughnut-shaped balloon structure, which is reusable.

In one embodiment, the mask is made of a relatively inexpensive plastic material and is disposable.

In another embodiment, the bite block is integrally formed with, or non releasably attached to, the mask body.

In yet another embodiment, the bite block is detachable from the mask body, so as to leave a large port to allow admission of one or more fingers or a sucker. This allows the mask to be removed from the patient whilst maintaining the bite block within the patient's mouth. The bite block is preferably detachably mounted to the face mask body in such a way as to allow the mask to be readily removable, leaving the bite block in the patient's mouth, if the face mask is removed in any situation, particularly in an emergency. The bite block preferably includes a clip area moulded to fit snugly into the face mask body so as to be able to seal out any oxygen escape and prevent loss of positive pressure during ventilation. The mask preferably includes a releasable, preferably clip on, cover to substantially seal the port in the absence of the bite block, to allow the mask to be used during colonoscopy.

The face mask preferably also includes one or more suctioning ports. Normally, a Yankeur sucker can be inserted through the bite block opening, through which an endoscope is inserted. Alternatively, an additional, smaller port directed at the nasal orifice can be included to allow insertion of a fine nasal suctioning catheter as required.

The face mask is preferably contoured to follow the nose and the upper lip and then wrap under the patient's lower lip or under the chin, and follow the shape of the face with the mouth open.

The face mask preferably also includes ports or openings to accommodate sensing devices. For example, the sensing devices can include pulse oximetry, respiratory rate measure, capnography or measurement of end-tidal $CO_2$ concentration (oral and nasal), which can in turn feed to a ventilator or other CPAP device with apnoea alarm triggering ventilation. Depth of inspiration/gas flow sensor and respiratory rate sensors can also be included. The face mask preferably also allows probe access therethrough allowing connection to the sensing devices, while a stick-on disposable pulse oximeter detector may be attached to the nose. Lip or earlobe oximetry is another alternative that can be used with the face mask.

BRIEF DESCRIPTION OF THE DRAWINGS

Preferred embodiments of the invention will now be described, by way of examples only, with reference to the accompanying drawings in which:

FIG. 1 is a front view of a first embodiment of a face mask;
FIG. 2 is a side view of the face mask shown in FIG. 1.

DETAILED DESCRIPTION OF THE PREFERRED EMBODIMENT

Figure 3:
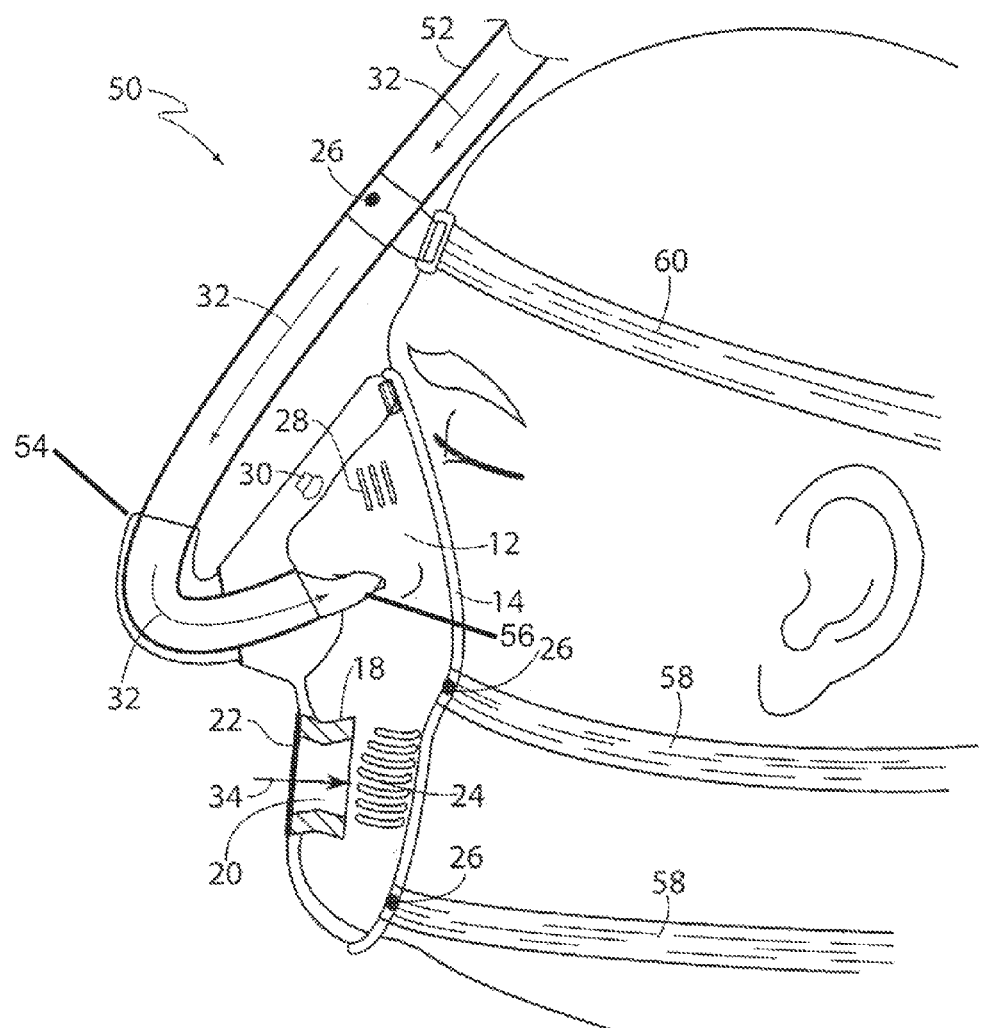
FIG. 3 is a side view of a second embodiment of a face mask, on a patient.

FIGS. 1 and 2 show a first embodiment of a face mask 10 for use with a patient undergoing a sedated endoscopic procedure. The face mask 10 allows the patient to lie on the left side of the body, as all endoscopic procedures are carried out with patients lying in the left lateral position. The face mask 10 includes a body 12 made of plastics material and shaped to cover the nose and mouth of a patient. The periphery of the body 12 is surrounded by a rubber seal 14 which, in use, forms a substantially airtight seal against the patient's skin.

The mask 12 also includes a means to provide positive airway pressure to the nose, in the form of a duct 16 which communicates with an aperture 17. The duct 16 is able to be connected to a powered (nasal) CPAP ventilating device or to a manual vent or bag ventilating device, such as a Leardal bag.

The mask 12 also includes a bite block 18 with an opening 20 therethrough. The bite block 18 is releasably attachable to the mask body 12 for disposal after use and replacement for a new patient. The bite block 18 also includes a one-way valve 22 across the opening 20 having an open position and a closed position. The one-way valve 20 is preferably in the form of resilient overlapping rubber segments forming a Heimlich-type valve. In the open position, the one-way valve allows passage of an endoscopic device into and through the opening 20. In the closed position, the one-way valve 22 substantially (airtight) seals the opening 20.

The mask 10 also includes corrugated expandable regions 24, which allow the region of the mask 10 near the bite block 18 to be expanded to the position shown in phantom line in order to allow mouth opening.

The mask 10 also includes four attachment points 26 suitable for connection to length adjustable or elastic straps in order to securely fix the mask 10 to the patient's face.

The mask 10 also includes expiratory outlets 28, and a $CO_2$ outlet 30 for capnography and pulse $0_2$ sensors 31.

In use, oxygen is delivered to the nose of the patient through the duct 16 and the aperture 17, as indicated by arrows 32. Simultaneously, an endoscope can be passed through the one-way valve 22 and into and through the opening 20 in the bite block 18, as indicated by arrow 34, to allow an endoscopic procedure to be conducted. The opening 20 is sized to be a snug, substantially airtight, seal with the exterior of the endoscope so that oxygen supplied via the duct 16 can not escape from the mask 10 through the opening 20 during the endoscopic procedure. The rubber seal 14 otherwise prevents oxygen from escaping from the mask 10 during use. The supply of oxygen can be continued after the endoscope has been removed from the opening 20 in the bite block 18, as the opening 20 is automatically closed and airtight sealed by the one-way valve 22.

FIG. 3 shows a second embodiment of a face mask 50. The face mask 50 has several features in common with the first embodiment of the face mask 10 previously described and such like features are indicated with like reference numerals. However, in the face mask 50, oxygen is supplied via a tube 52 which enters the mask body 12 at region 54 and terminates in a pair of nasal cannula 56. FIG. 3 also shows mask straps 58 and an additional strap 60 which locates the tube 52.

Figure 4:
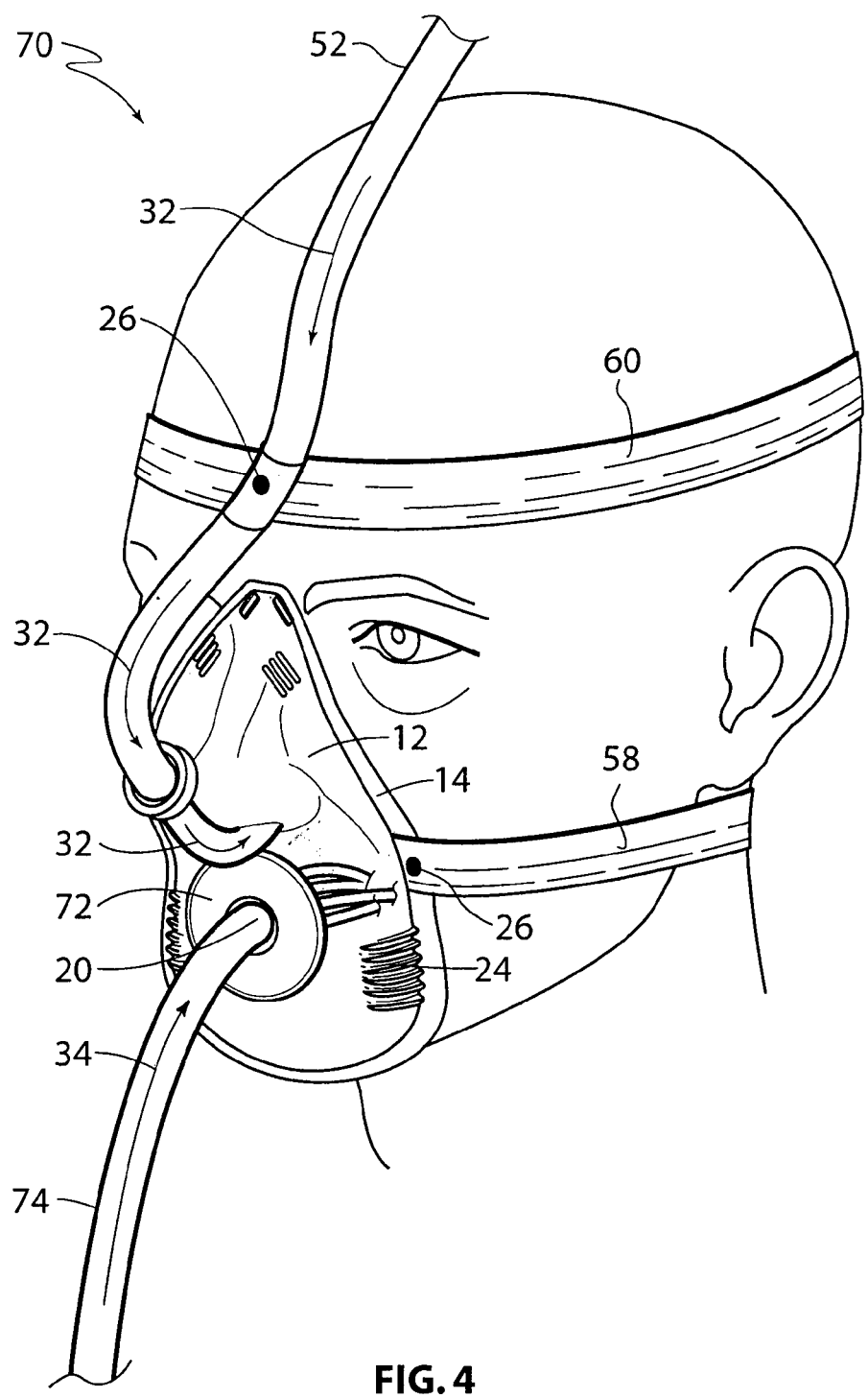
FIG. 4 is a perspective view of a third embodiment of a face mask, on a patient.

FIG. 4 shows a third embodiment of a face mask 70. The face mask 70 has several features in common with the first and second embodiments of the face masks 10 and 50 previously described and such like features are indicated with like reference numerals. However, the face mask 70 includes a one-way valve in the form of a doughnut-shaped balloon structure 72. FIG. 4 also shows an endoscope 74 inserted through the opening 20 of the bite block 18 via the one-way valve 72.

The main advantages provided by the face masks 10, 50 and 70 include: (1) the ability to create a pre-oxygenation capacity to abolish hypoxic 'dip' (as will be described in more detail below); (2) the ability to deliver positive nasal CPAP pressure ventilation to overcome the common iatrogenic 'sleep apnoea'; and (3) the one-way valve access to the bite block opening preventing escape of insufflated gases from the mouth during endoscopy. Additional advantages include: (4) the allowance of continuous sensing of various vital parameters; (5) suction and dilatation access; (6) hands-free operation due to the face mask being strapped to the patient; (6) the ability to continue using the face mask during colonoscopy which may follow gastroscopy; (7) the ability to pass an endoscope through the mask without appreciable loss of intra-mask pressure, which can also facilitate oesophageal dilatation; and (8) the ability to allow fluid top be aspirated from the patient's lungs through the larynx or to aspirate secretions from the pharynx.

How the masks 10, 50 and 70 described above advantageously permit the ventilation of over-sedated patients during gastroscopic/bronchoscopic procedures and overcome early hypoxic 'dip', is as follows. The natural history of oxygen saturation during sedation pre-endoscopy is characterized by a flat oxygen tension line close to 100% saturation which then dips to a nadir of around 88-92% as the patient is induced with agents such as midazolam and propofol. With larger doses of sedative, the dip in oxygen saturation can reach levels of 70-90%. With standard, low doses of sedative that do not reach a de-saturation of 90%, the entire saturation dip does not last any more than around one minute. The masks 10, 50 and 70 advantageously overcome the early oxygen de-saturation trough through preoxygenation and allow a constant level of oxygen saturation of between 95% and 100% to be maintained. Further, the masks 10, 50 and 70 advantageously permit 100% pre-oxygenation before endoscopy leading to nitrogen wash out. This creates a reservoir of oxygen within the patient to help tide the patient over the usual transient, early sedation dip in oxygen tension as described above. Instead of reaching a deep nadir of say 80% saturation, the patient can maintain a saturation close to 100% for 1 to 3 minutes and at times longer than that. A large proportion of endoscopy procedure time would be completed by 3-5 minutes and hence assisted ventilation would be required in those with either prolonged procedures or patients with clinically dangerous, hypoxia-prone conditions.

The masks 10, 50 and 70 also advantageously allow ventilation of patients, with the option of manually ventilating (e.g. using a Leardal bag mask) or the option of commercially available CPAP devices, which can automatically augment ventilation or ventilate patients during times of deeper sedation as inbuilt sensing devices determine the need and time to ventilate without gas loss through the mouth.

Although the invention has been described with reference to preferred embodiments, it will be appreciated by persons skilled in the art that the invention may be embodied in many other forms.

The invention claimed is:

1. A face mask for a patient undergoing a sedated endoscopic procedure, the face mask comprising:
    an aperture to provide positive airway pressure to a nose of a patient;
    a bite block with an opening therein;
    two corrugated regions positioned on opposite sides of the bite block, each corrugated region configured to expand a respective portion of the face mask near the bite block to permit opening of a mouth of the patient; and
    a one-way valve having an open position, configured to allow passage of an endoscopic device therethrough and into the opening, and a closed position substantially sealing the opening.

2. The face mask as claimed in claim 1, wherein the face mask includes a body configured to cover the patient's nose and mouth in a substantially sealed relationship with the patient's skin.

3. The face mask as claimed in claim 2, wherein the aperture is attached to, or forms part of, the body.

4. The face mask as claimed in claim 1, wherein the face mask includes a first body configured to cover the patient's nose in a substantially sealed relationship with the patient's skin and a second body configured to cover the patient's mouth in a substantially sealed relationship with the patient's skin.

5. The face mask as claimed in claim 4, wherein the aperture is attached to, or forms part of, the first body and the bite block is attached to, or forms part of, the second body.

6. The face mask as claimed in claim 1, wherein the mask includes one or more straps for securing the mask to the patient's head.

7. The face mask as claimed in claim 6, wherein the straps are length adjustable or elastic, in order to allow the mask to be pressed against the patient's skin to improve sealing.

8. The face mask as claimed in claim 6, wherein the one or more straps comprise a first strap for securing the mask to a top portion of the patient's head and for locating the tube, and at least one second strap for securing the mask to a bottom portion of the patient's head.

9. The face mask as claimed in claim 1, wherein the mask includes one or more sealing elements around its periphery configured to form a substantially sealed relationship with the patient's skin.

10. The face mask as claimed in claim 9, wherein the sealing element includes a hollow, tubular rubber rim or multiple soft rubber rims.

11. The face mask as claimed in claim 1, wherein the aperture is adapted for fluid communication with a manual source or an automated source of positive pressure.

12. The face mask as claimed in claim 11, wherein the aperture is adapted to provide the positive airway pressure to the nose via a CPAP device used as a passively ventilating nasal system with manual and automatic CPAP override.

13. The face mask as claimed in claim 1, wherein the bite block opening is configured to accommodate an endoscope.

14. The face mask as claimed in claim 1, wherein the bite block is disposable or reusable.

15. The face mask as claimed in claim 1, wherein the one-way valve includes a substantially circular doughnut-like balloon.

16. The face mask as claimed in claim 1, wherein the one-way valve is a rubber membrane with a central round opening sized to admit an endoscope.

17. The face mask as claimed in claim 16, wherein the rubber membrane opening is of a size just smaller than an endoscope.

18. The face mask as claimed in claim 16, wherein the rubber membrane opening is of a size to suit instruments larger than an endoscope.

19. The face mask as claimed in claim 16, wherein the opening is lubricated.

20. The face mask as claimed in claim 16, wherein the one-way valve is a fixed doughnut-shaped balloon structure, which is reusable.

21. The face mask as claimed in claim 1, wherein the mask is made of a plastic material and is disposable.

22. The face mask as claimed in claim 1, wherein the face mask comprises a mask body, and wherein the bite block is integrally formed with, or non releasably attached to, the mask body.

23. The face mask as claimed in claim 1, wherein the face mask comprises a mask body, and wherein the bite block is detachable from the mask body, so as to leave a large port to allow admission of one or more fingers or a sucker.

24. The face mask as claimed in claim 23, wherein the bite block includes a clip area moulded to fit snugly into the face mask body so as to be able to seal out any oxygen escape and prevent loss of positive pressure during ventilation.

25. The face mask as claimed in claim 1, wherein the face mask comprises a mask body, and wherein the bite block is detachably mounted to the mask body in such a way as to allow the mask to be readily removable, leaving the bite block in the patient's mouth, if the face mask is removed.

26. The face mask as claimed in claim 1, wherein the mask includes a releasable cover to substantially seal the opening in the absence of the bite block, to allow the mask to be used during colonoscopy.

27. The face mask as claimed in claim 26, wherein the releasable cover is a clip on cover.

28. The face mask as claimed in claim 1, wherein the face mask includes one or more suctioning ports.

29. The face mask as claimed in claim 1, wherein the face mask is contoured to follow the nose and the upper lip and then wrap under the patient's lower lip or under the chin, and follow the shape of the face with the mouth open.

30. The face mask as claimed in claim 1, wherein the face mask includes ports or openings to accommodate sensing devices.

31. The face mask as claimed in claim 30, wherein the sensing devices include pulse oximetry, respiratory rate measure, capnography or measurement of end-tidal $CO_2$ concentration.

32. The face mask as claimed in claim 30, wherein the sensing devices include a depth of inspiration/gas flow sensor or respiratory rate sensor.

33. The face mask as claimed in claim 30, wherein the face mask is configured to permit probe access therethrough allowing connection to the sensing devices.

34. The face mask as claimed in claim 1, wherein the aperture is positioned in a central region of the face mask to be aligned, in use, with the nose of the patient.

35. The face mask as claimed in claim 1, wherein the mask is adapted to attach to a duct external to the mask, wherein the aperture is adapted to communicate with the duct to provide the positive airway pressure to the nose of the patient, and wherein the duct is elbow-shaped.

* * * * *